United States Patent
Okuda

(10) Patent No.: US 11,058,558 B2
(45) Date of Patent: Jul. 13, 2021

(54) MULTI-ARTICULATED LINK KNEE JOINT

(71) Applicant: NABTESCO CORPORATION, Tokyo (JP)

(72) Inventor: Masahiko Okuda, Hyogo (JP)

(73) Assignee: NABTESCO CORPORATION, Tokyo (JP)

( * ) Notice: Subject to any disclaimer, the term of this patent is extended or adjusted under 35 U.S.C. 154(b) by 41 days.

(21) Appl. No.: 16/381,420

(22) Filed: Apr. 11, 2019

(65) Prior Publication Data
US 2019/0314173 A1 Oct. 17, 2019

(30) Foreign Application Priority Data
Apr. 11, 2018 (JP) .............................. JP2018-076108

(51) Int. Cl.
*A61F 2/64* (2006.01)
*A61F 2/68* (2006.01)
*A61F 2/70* (2006.01)
*A61F 2/76* (2006.01)
*A61F 2/50* (2006.01)

(52) U.S. Cl.
CPC ................ *A61F 2/644* (2013.01); *A61F 2/70* (2013.01); *A61F 2/76* (2013.01); *A61F 2002/5006* (2013.01); *A61F 2002/5084* (2013.01); *A61F 2002/6863* (2013.01); *A61F 2002/704* (2013.01); *A61F 2002/762* (2013.01); *A61F 2002/7625* (2013.01)

(58) Field of Classification Search
CPC .. A61F 2/64; A61F 2/642; A61F 2/644; A61F 2/68; A61F 2/70; A61F 2002/6818; A61F 2002/6863; A61F 2002/74
See application file for complete search history.

(56) References Cited

U.S. PATENT DOCUMENTS

| | | | |
|---|---|---|---|
| 5,383,939 A | 1/1995 | James | |
| 6,113,642 A | 9/2000 | Petrofsky et al. | |
| 7,066,964 B2 | 6/2006 | Wild | |
| 9,532,877 B2 * | 1/2017 | Holgate | A61F 2/66 |
| 9,987,152 B2 * | 6/2018 | Chabloz | A61F 2/64 |
| 10,039,652 B2 * | 8/2018 | Zahedi | A61F 2/6607 |
| 10,624,766 B2 * | 4/2020 | Battlogg | A61F 2/70 |
| 2004/0193286 A1 | 9/2004 | Grundei | |
| 2008/0039756 A1 | 2/2008 | Thorsteinsson et al. | |
| 2015/0032228 A1 | 1/2015 | Shirata et al. | |

FOREIGN PATENT DOCUMENTS

WO 2013132662 A1 9/2013

OTHER PUBLICATIONS

USPTO Non-Final Office Action in U.S. Appl. No. 16/380,227; dated: Dec. 4, 2020.

* cited by examiner

*Primary Examiner* — Bruce E Snow
(74) *Attorney, Agent, or Firm* — Cantor Colburn LLP

(57) ABSTRACT

A multi-articulated link knee joint includes: a knee unit in which an upper link unit rotates relative to a lower link unit by a multi-articulated link mechanism including a plurality of link units including the upper link unit and the lower link unit; a cylinder device for assisting the motion of the knee unit and moving in accordance with the rotation of the upper link unit; a position detector for detecting the distance from the lower link unit to the cylinder device; and an angle detector for obtaining the bending angle of the knee unit from the detected distance from the cylinder device.

2 Claims, 13 Drawing Sheets

MULTI-ARTICULATED LINK KNEE JOINT

CROSS REFERENCE TO RELATED APPLICATION

The present application claims priority under 35 U.S.C. § 119 to Japanese Application No. 2018-076108, filed Apr. 11, 2018, the entire content of which is incorporated herein by reference.

BACKGROUND OF THE INVENTION

1. Field of the Invention

The present invention relates to a multi-articulated link knee joint.

2. Description of the Related Art

Prosthetic legs used by people who had have their thigh cut above their knee due to a disease or an accident are coupled with an artificial knee joint that bends like a knee joint of a living body. When the artificial knee joint is bent depending on the motion of the user, motions such as standing, sitting, and walking are made possible.

WO2013/132662 discloses an artificial knee joint including a knee unit that is bent by a multi-articulated link mechanism and a fluid cylinder as an auxiliary driver that assists the motion of the knee unit depending on the bending angle. In this artificial knee joint, since the multi-articulated link mechanism allows the motion of the knee unit to be similar to that of the knee joint of a living body, more natural motion is made possible. In addition, since walking motion is supported by a fluid cylinder, the stability of walking is improved.

In the knee joint according to Patent document 1, a magnetic sensor is provided at a cylinder tube of a fluid cylinder, and a magnet is provided inside a piston rod of the fluid cylinder, which enables detection of the position of the piston rod relative to the cylinder tube. The bending angle of the knee unit is obtained on the basis of the position of the piston rod to control the characteristics of the fluid cylinder.

However, the knee joint according to Patent document 1 requires a special fluid cylinder in which a magnet is built in the piston rod, and thus the price tends to be expensive.

SUMMARY OF THE INVENTION

The present invention has been made in view of the above disadvantage, and an object of the present invention is to provide a multi-articulated link knee joint capable of detecting a bending angle of a knee unit with a reasonable configuration.

One embodiment of the present invention is a multi-articulated link knee joint. This multi-articulated link knee joint includes: a knee unit in which an upper link unit rotates relative to a lower link unit by a multi-articulated link mechanism including a plurality of link units including the upper link unit and the lower link unit; an auxiliary driver for assisting the motion of the knee unit and moving in accordance with rotation of the upper link unit; a position detector for detecting the relative position of the auxiliary driver relative to the lower link unit; and an angle detector for obtaining the bending angle of the knee unit from the detected relative position of the auxiliary driver.

According to this embodiment, since the relative position of the auxiliary driver relative to the lower link unit is detected and the bending angle of the knee unit is obtained from the detection result, it is not necessary to use a special auxiliary driver, and the bending angle of the knee unit can be detected with a reasonable configuration.

BRIEF DESCRIPTION OF THE DRAWINGS

The invention will now be described by reference to the preferred embodiments. This does not intend to limit the scope of the present invention, but to exemplify the invention.

DETAILED DESCRIPTION OF THE INVENTION

Figure 1:
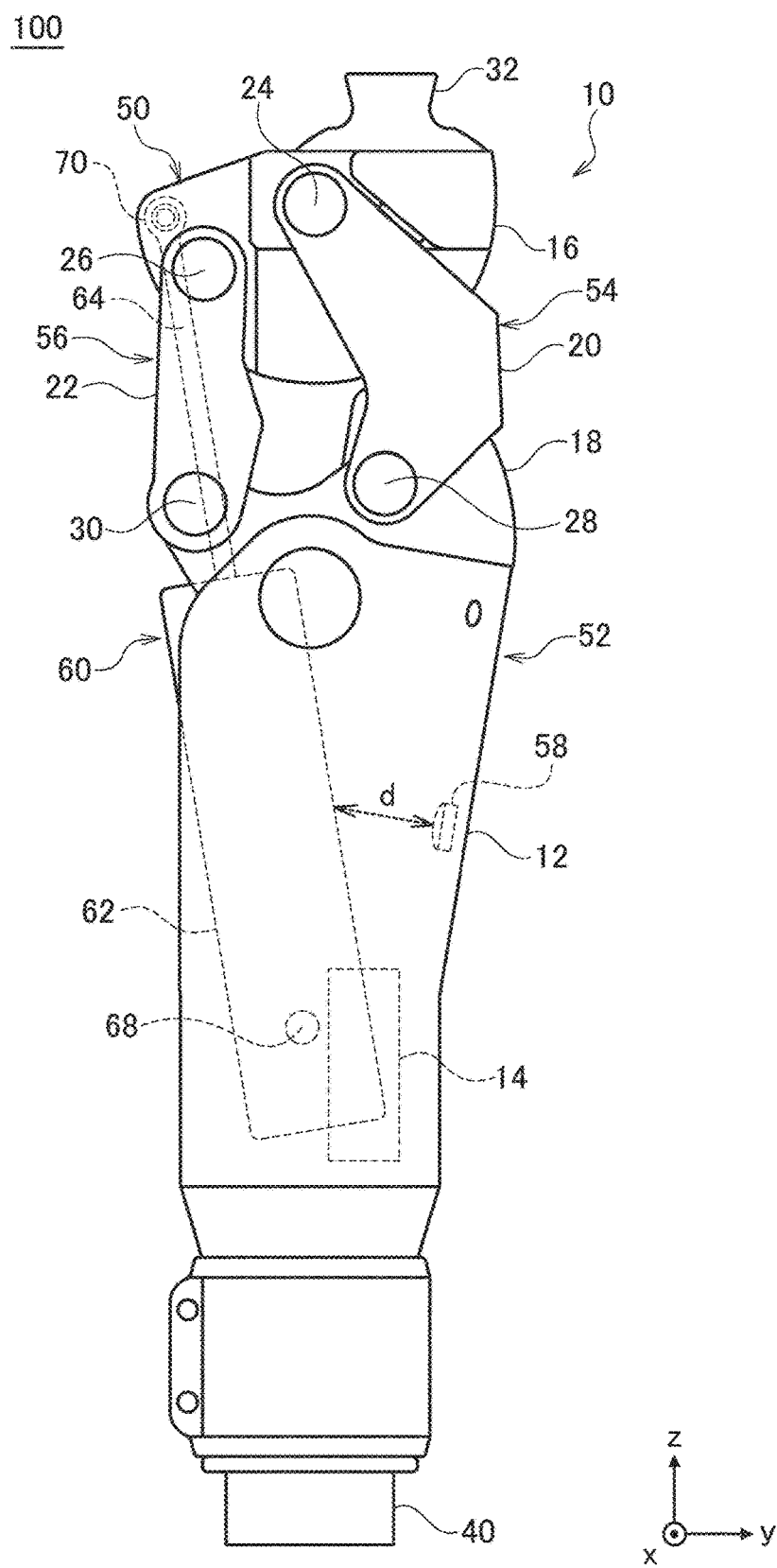
FIG. 1 is a side view of a multi-articulated link knee joint according to a first embodiment of the present invention.

Hereinafter, in embodiments, the same component is denoted by the same symbol, and redundant explanations are omitted. In addition, for convenience of explanation, a part of a component is omitted as appropriate in the drawings.

Before specifically explaining a multi-articulated link knee joint according to an embodiment, the overview will be explained. A multi-articulated link knee joint according to an embodiment includes a knee unit in which an upper link unit rotates with respect to a lower link unit by a multi-articulated link mechanism and an auxiliary driver for assisting the motion of the knee unit. The auxiliary driver moves in accordance with the rotation of the upper link unit. The auxiliary driver may be, for example, a cylinder device or a rotary damper. The multi-articulated link knee joint includes a position detector for detecting the relative position of the auxiliary driver relative to the lower link unit. The relative position of the auxiliary driver may be, for example, the distance from the lower link unit to the auxiliary driver, the inclination angle of the auxiliary driver with respect to the lower link unit, the rotation angle of the auxiliary driver with respect to the lower link unit, and so on. The bending angle of the knee unit can be detected from the detected relative position of the auxiliary driver.

Figure 2:
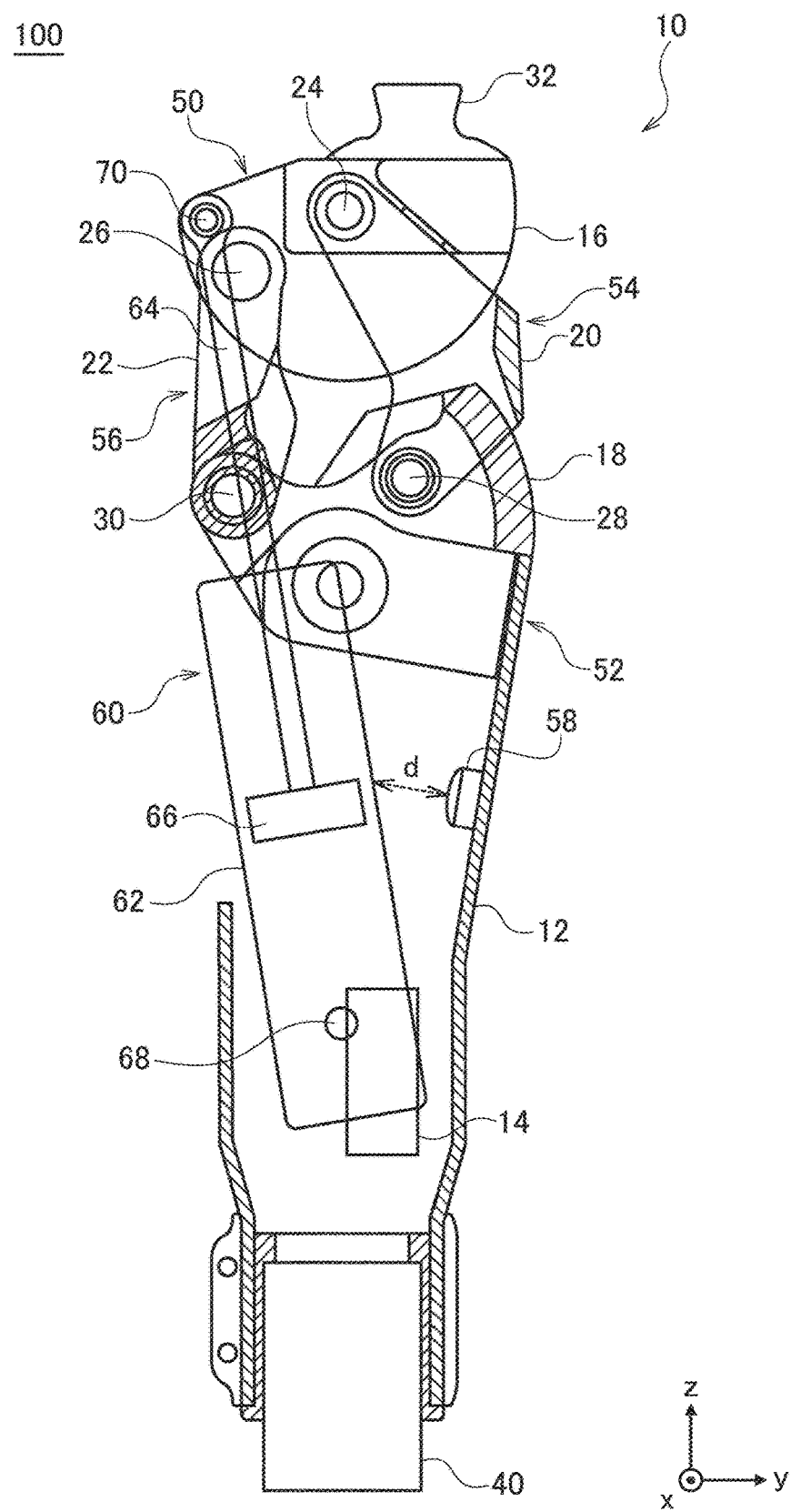
FIG. 2 is a schematic cross-sectional view of the multi-articulated link knee joint according to the first embodiment of the present invention.
Figure 3:
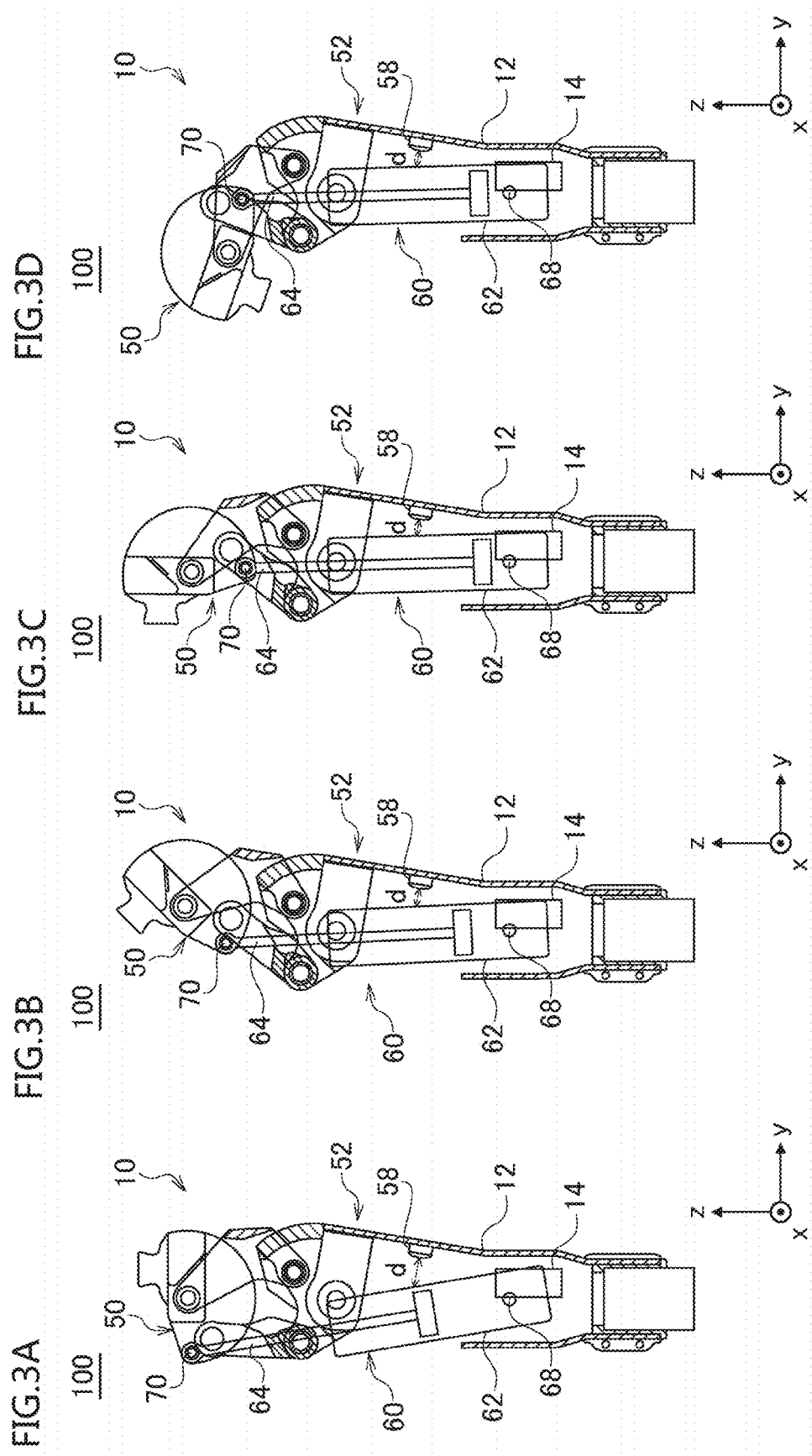
FIG. 3A to FIG. 3D are views illustrating how a knee unit is bent in the multi-articulated link knee joint according to the first embodiment.

FIG. 1 is a side view of a multi-articulated link knee joint 100 according to a first embodiment of the present invention. FIG. 2 is a schematic cross-sectional view of the multi-articulated link knee joint 100 according to the first embodiment of the present invention. In the following description, in an xyz orthogonal coordinate system illustrated in each drawing, a direction parallel to the x axis is defined as the lateral direction, and the positive direction of the x axis is referred to as "left" with the negative direction referred to as "right." A direction parallel to the y axis is defined as the anterior-posterior direction, and the positive direction of the y axis is referred to as "anterior" with the negative direction referred to as "posterior." A direction parallel to the z axis is defined as the vertical direction, and the positive direction of the z axis is referred to as "up" with the negative direction referred to as "down."

The multi-articulated link knee joint 100 includes a knee unit 10. The knee unit 10 is bent by a multi-articulated link mechanism having a plurality of link units. In the first embodiment, the multi-articulated link mechanism includes four link units of an upper link unit 50, a lower link unit 52, an anterior link unit 54, and a posterior link unit 56. In this specification, a link and parts secured to the link to move in conjunction with the link are collectively referred to as a "link unit." The upper link unit 50 includes an upper link 16 and a thigh connector 32. The lower link unit 52 includes a lower link 18 and an lower leg part 12. The anterior link unit 54 includes an anterior link 20. The posterior link unit 56 includes a posterior link 22.

The upper link 16 is provided with a first shaft 24 and a second shaft 26, and the lower link 18 is provided with a third shaft 28 and a fourth shaft 30. Each of the shafts is provided such that the axial direction thereof is parallel to the x axis and so as to be rotatable. The anterior link 20 is attached to the ends of the first shaft 24 and the third shaft 28. The posterior link 22 is attached to the ends of the second shaft 26 and the fourth shaft 30. The upper link 16 is supported by the anterior link 20 and the posterior link 22 and rotates with respect to the lower link 18. A thigh connector 32 protruding from the upper link 16 is connected to a socket attached to the thigh of a user. An angle formed by the direction in which the thigh connector 32 protrudes and the z axis is defined as the bending angle of the knee unit 10. The bending angle illustrated in FIG. 1 and FIG. 2 is 0°, which is a state in which the knee unit 10 is completely extended.

The lower leg part 12 is formed in a cylindrical shape and is secured under the lower link 18. Furthermore, provided under the lower leg part 12 is a leg connector 40 which is connected to a leg part included in a prosthetic leg.

The multi-articulated link knee joint 100 further includes a cylinder device 60 as an auxiliary driver that assists the motion of the knee unit 10. The cylinder device 60 may be an air cylinder or a hydraulic cylinder.

The cylinder device 60 includes a cylinder tube 62, a piston rod 64 movable relative to the cylinder tube 62, and a piston 66 movably accommodated in the cylinder tube 62 and secured to the piston rod 64. The cylinder device 60 is provided so as to couple the upper link unit 50 and the lower link unit 52. More specifically, the cylinder tube 62 is rotatably supported by a lower shaft 68 provided at the lower leg part 12 of the lower link unit 52, and the piston rod 320 is rotatably supported by an upper shaft 70 provided at the upper link 16 of the upper link unit 50. The cylinder device 60 provided in the above manner moves in the anterior-posterior direction about the lower shaft 68 in accordance with the rotation of the upper link unit 50.

The multi-articulated link knee joint 100 further includes a position detector 58. The position detector 58 is installed in the lower leg part 12 and measures the distance d from the cylinder device 60 to the lower leg part 12. The position detector 58 is not particularly limited as long as detection of the distance d to the cylinder device 60 can be performed. For example, an infrared sensor can be used. Alternatively, a magnet may be attached to the outer surface of the cylinder tube 62, and the distance d may be detected using a Hall element as the position detector 58.

FIG. 3A to FIG. 3D are views illustrating how the knee unit 10 is bent in the multi-articulated link knee joint 100 according to the first embodiment. The bending angles of the knee unit 10 illustrated in FIG. 3A to FIG. 3D are 0°, 45°, 90°, and 160°, respectively. When the bending angle is large, the anterior link 20 and the posterior link 22 intersect. The upper link 16 rotates while moving backward with respect to the lower link 18. Due to the rotation of the upper link 16, the knee unit 10 bends like the knee joint of a living body does.

As described above, the piston rod 64 of the cylinder device 60 is rotatably supported by the upper shaft 70 of the upper link 16, and the cylinder tube 62 of the cylinder device 60 is rotatably supported by the lower shaft 68 of the lower leg part 12. Therefore, the distance d from the cylinder device 60 to the lower leg part 12 varies in accordance with a change in the bending angle of the knee unit 10, that is, the rotation of the upper link 16. As can be understood from FIG. 3A to FIG. 3D, in the multi-articulated link knee joint 100 according to the first embodiment, the distance d from the lower leg part 12 to the cylinder device 60 decreases as the bending angle of the knee unit 10 increases.

The multi-articulated link knee joint 100 further includes a control device 14. The control device 14 is accommodated in the lower leg part 12. The control device 14 receives a detection value of the position detector 58, obtains the bending angle of the knee unit 10 from the detection value, and controls the cylinder device 60.

Figure 4:
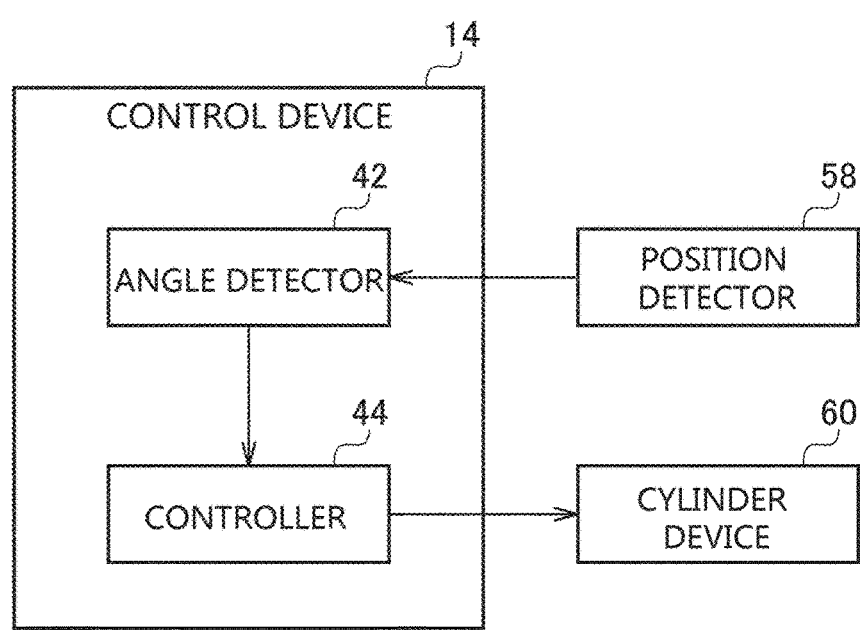
FIG. 4 is a block diagram illustrating a functional configuration of a control device.

FIG. 4 is a block diagram illustrating a functional configuration of the control device 14. Each of the blocks illustrated herein in the block diagram can be implemented by an element or a mechanical device including a CPU of a computer from the perspectives of hardware and, from the perspectives of software, by a computer program or the like. In this example, functional blocks implemented by coordination thereof are illustrated. Therefore, it should be understood by a person skilled in the art that these functional blocks can be implemented by various forms by hardware, software, or a combination thereof.

The control device 14 includes an angle detector 42 and a controller 44. The angle detector 42 obtains the bending angle of the knee unit 10 from the detection value of the position detector 58. For example, when a table is generated in advance by measuring the relationship between the bending angle of the knee unit 10 and the detection value of the position detector 58, a bending angle of the knee unit 10 can be obtained from a detection value of the position detector 58 by referring to the table.

The controller 44 controls the cylinder device 60 in accordance with the bending angle to assist the motion of the knee unit 10. The controller 44 controls the cylinder device 60 so as to limit the rotation of the third shaft 28 at the time of standing when the bending angle is close to 0°. This prevents knee bending, that is, the knee unit 10 bent against the will of the user. In addition, when the leg is in a swinging state in which the bending angle changes such as at the time of walking, the cylinder device 60 is controlled to rotate the third shaft 28 in accordance with the angle-changing direction. As a result, the lower leg part 12 swings in accordance with kicking-out of the leg, and thus the user can walk comfortably.

The usage and operation according to the above configuration are as follows. The multi-articulated link knee joint 100 is used while the thigh connector 32 is connected to a socket attached to the thigh of the user with the leg part connected to the leg connector 40. The knee unit 10 bends when the upper link 16 rotates with respect to the lower link 18 by the multi-articulated link mechanism. When the knee unit 10 is bent, the angle detector 42 obtains the bending angle from the detection value of the position detector 58. The controller 44 controls the cylinder device 60 in accordance with the bending angle to assist the motion of the knee unit 10.

In the multi-articulated link knee joint 100 according to the first embodiment, the position detector 58 is provided at the lower link unit 52 (more specifically, the lower leg part 12) to measure the distance d from the lower link unit 52 (more specifically, the lower leg part 12) to the cylinder device 60 to obtain the bending angle of the knee unit 10 on the basis of this distance d. Therefore, it is not necessary to use a special device, such as a piston rod in which a magnet is incorporated, as the cylinder device 60, and thus the bending angle of the knee unit 10 can be detected with a relatively reasonable configuration.

In the multi-articulated link knee joint 100 according to the first embodiment, both the position detector 58 and the angle detector 42 (control device 14) are provided at the lower link unit 52. Since the angle detector 42 obtains the bending angle of the knee unit 10 from the detection result of the position detector 58, in order to transmit detection information of the position detector 58 to the angle detector 42, it is necessary that the position detector 58 and the angle detector 42 be connected by wiring. In the case where the position detector 58 and the angle detector 42 are provided at separate portions that are displaced from each other, it is necessary to adopt a structure that does not cause a failure such as disconnection in the wiring. This is not preferable since this leads to increased cost of the knee joint. On the other hand, in the multi-articulated link knee joint 100 according to the first embodiment, since the position detector 58 and the angle detector 42 (control device 14) are provided at the same lower link unit, wiring can be simplified. This results in cost reduction of the knee joint.

In the first embodiment described above, the position detector 58 is provided at the lower leg part 12; however, the position detector 58 may be provided at the lower link 18.

Figure 5:
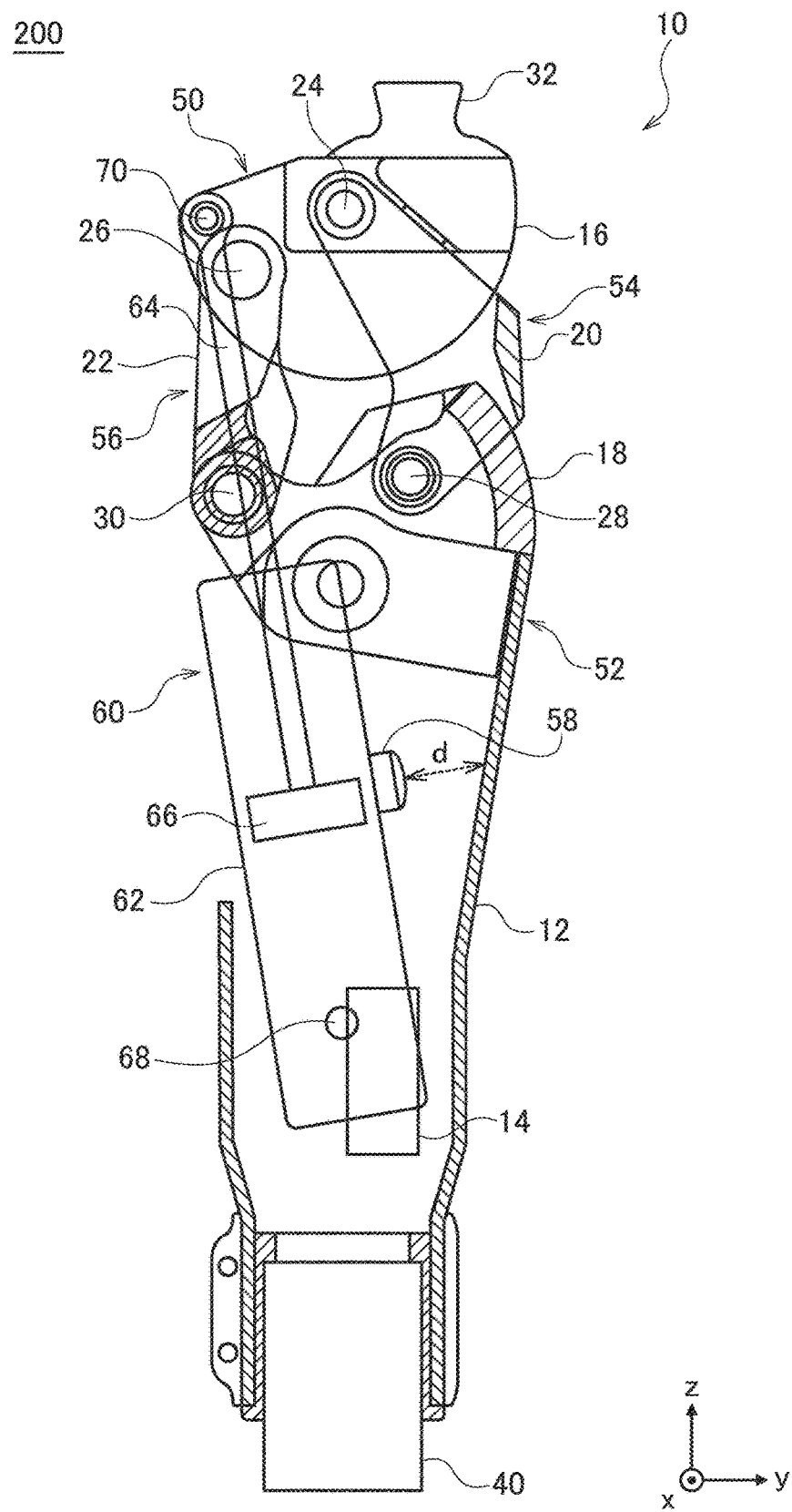
FIG. 5 is a schematic cross-sectional view of a multi-articulated link knee joint according to a second embodiment of the present invention.

FIG. 5 is a schematic cross-sectional view of a multi-articulated link knee joint 200 according to the second embodiment of the present invention. The multi-articulated link knee joint 200 illustrated in FIG. 5 is different from the multi-articulated link knee joint 100 according to the first embodiment in that a position detector 58 is provided at the outer surface of a cylinder tube 62 of a cylinder device 60. Also in the second embodiment, the position detector 58 measures the distance d from the cylinder device 60 to a lower link unit 52, and an angle detector 42 of a control device 14 obtains the bending angle of a knee unit 10 on the basis of the distance d.

Also in the multi-articulated link knee joint 200 according to the second embodiment, since it is not necessary to use a special device as the cylinder device 60, the bending angle of the knee unit 10 can be detected with a relatively reasonable configuration.

In the second embodiment, the control device 14 is provided at an lower leg part 12; however, the control device 14 may be provided at the cylinder device 60. In this case, since the position detector 58 and the control device 14 are provided at the same portion, the wiring connecting the two can be simplified.

Figure 6:
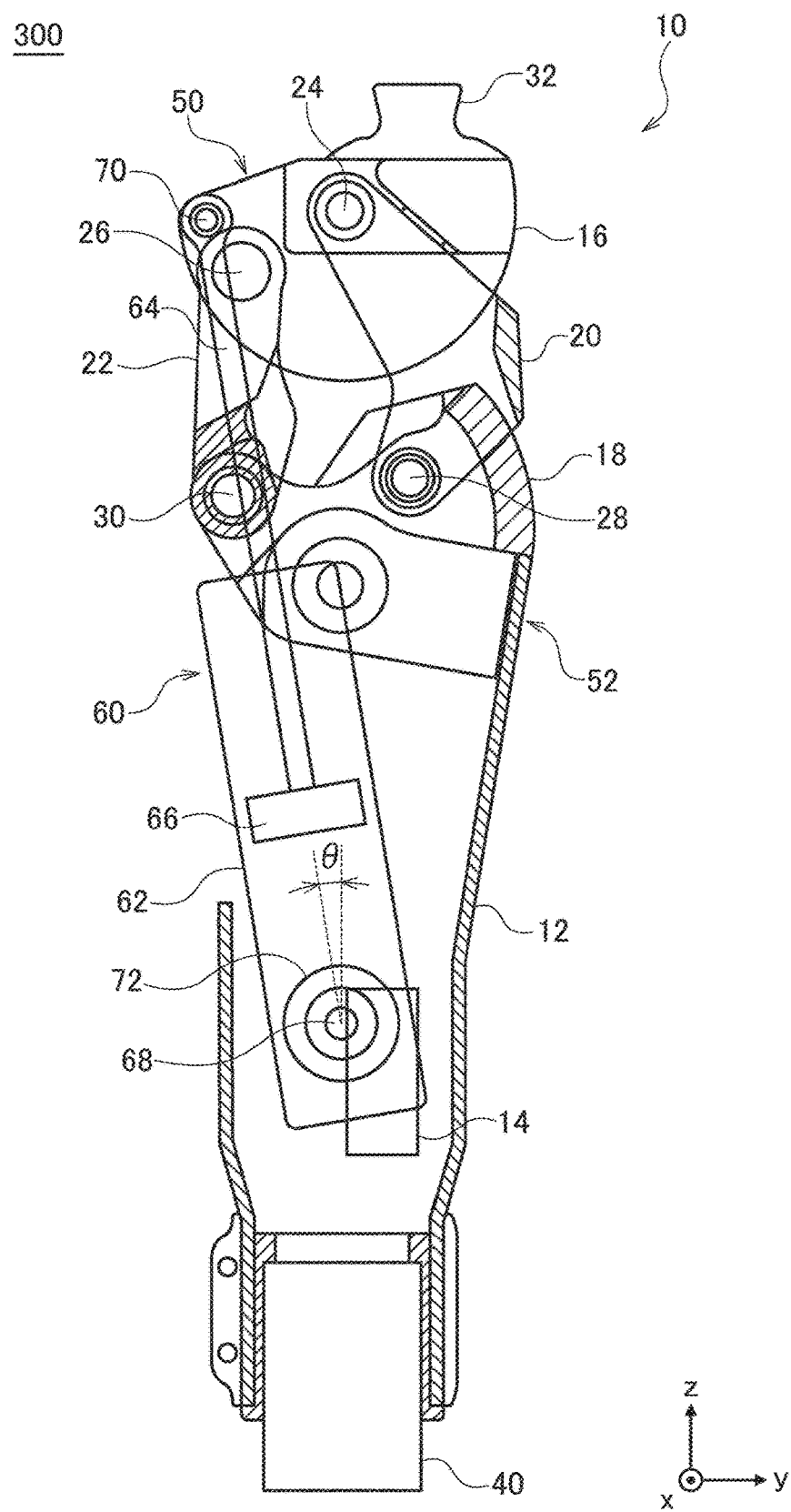
FIG. 6 is a schematic cross-sectional view of a multi-articulated link knee joint according to a third embodiment of the present invention.
Figure 7:
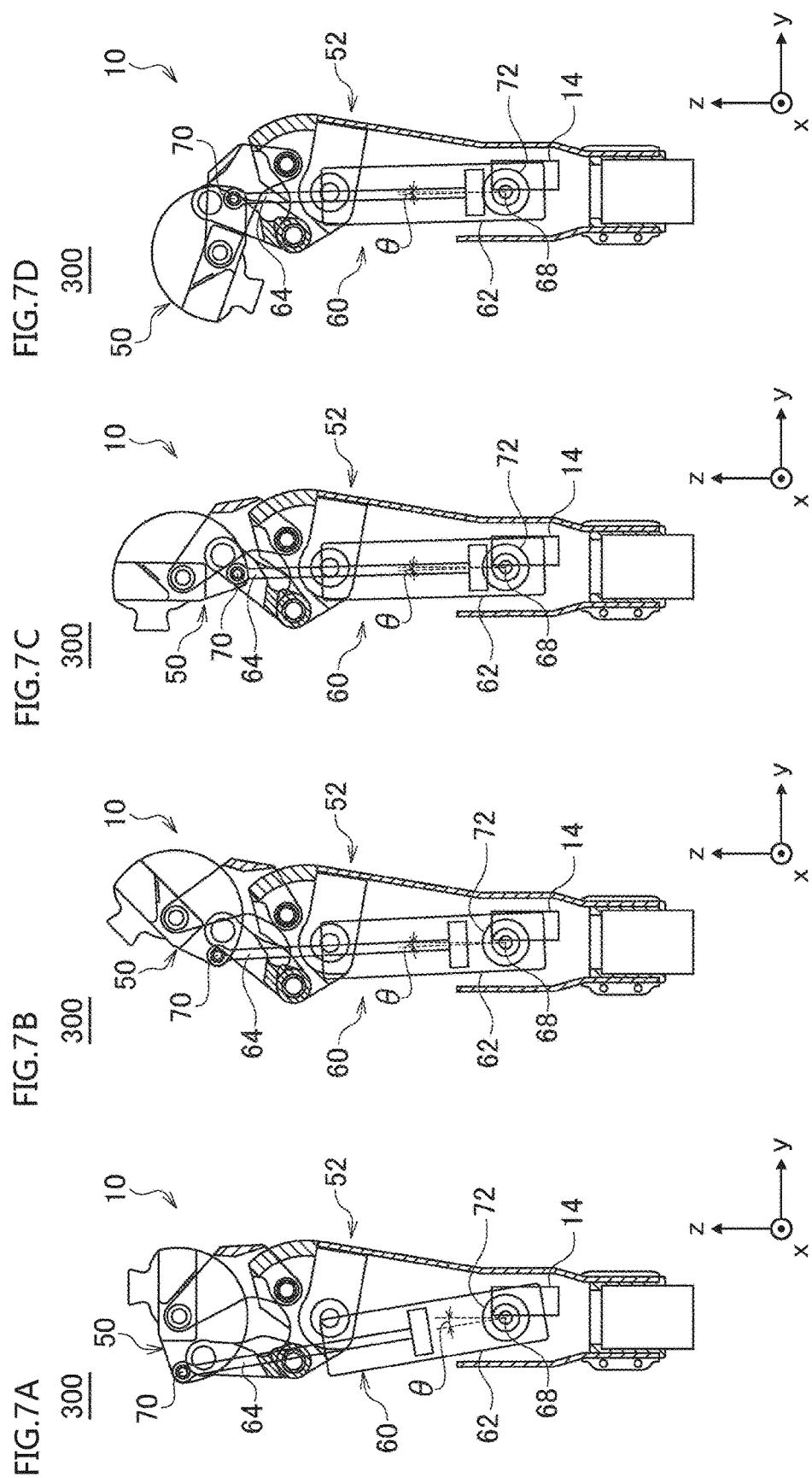
FIG. 7A to FIG. 7D are views illustrating how a knee unit is bent in the multi-articulated link knee joint according to the third embodiment.

FIG. 6 is a schematic cross-sectional view of a multi-articulated link knee joint 300 according to a third embodiment of the present invention. The multi-articulated link knee joint 300 according to the third embodiment is different from the multi-articulated link knee joint 100 according to the first embodiment in the configuration of a rotation detector 236. Specifically, in the multi-articulated link knee joint 300, a position detector 72 is configured and arranged so as to detect the inclination angle θ of a cylinder device 60 with respect to a lower link unit 52. In this example, the angle formed by the longitudinal direction of the cylinder device 60 (in other words, expansion/contraction direction of a piston rod 64) and the z axis is regarded as the inclination angle θ of the cylinder device 60.

In the third embodiment, the position detector 72 is attached to an lower leg part 12. As the position detector 72, for example, a potentiometer, a rotary encoder, a resolver, or the like can be used.

FIG. 7A to FIG. 7D are views illustrating how the knee unit 10 is bent in the multi-articulated link knee joint 300 according to the third embodiment. The bending angles of the knee unit 10 illustrated in FIG. 7A to FIG. 7D are 0°, 45°, 90°, and 160°, respectively. The inclination angle θ of the cylinder device 60 with respect to the lower leg part 12 changes in accordance with the change in the bending angle of the knee unit 10. In the multi-articulated link knee joint 300 according to the third embodiment, as the bending angle of the knee unit 10 increases, the inclination angle θ of the cylinder device 60 with respect to the lower leg part 12 decreases.

The angle detector 42 (see FIG. 4) of the control device 14 obtains the bending angle from a detection value of the position detector 72. For example, when a table is generated in advance by measuring the relationship between the bending angle of the knee unit 10 and the detection value of the position detector 72, a bending angle of the knee unit 10 can be obtained from a detection value of the position detector 72 by referring to the table. The controller 44 (see FIG. 4) controls the cylinder device 60 in accordance with the bending angle to assist the motion of the knee unit 10.

Also in the multi-articulated link knee joint 300 according to the third embodiment, since it is not necessary to use a special device as the cylinder device 60, the bending angle of the knee unit 10 can be detected with a relatively reasonable configuration.

Moreover, in the multi-articulated link knee joint 300 according to the third embodiment, since the position detector 72 and the angle detector 42 (control device 14) are provided at the same portion (lower leg part 12), the wiring can be simplified.

In the third embodiment described above, the position detector 72 is attached to the lower leg part 12 to detect the inclination angle of the cylinder device 60 with respect to the lower leg part 12; however, the position detector 72 may be attached to the cylinder device 60 to detect the inclination angle of the cylinder device 60 with respect to the lower leg part 12.

Figure 8:
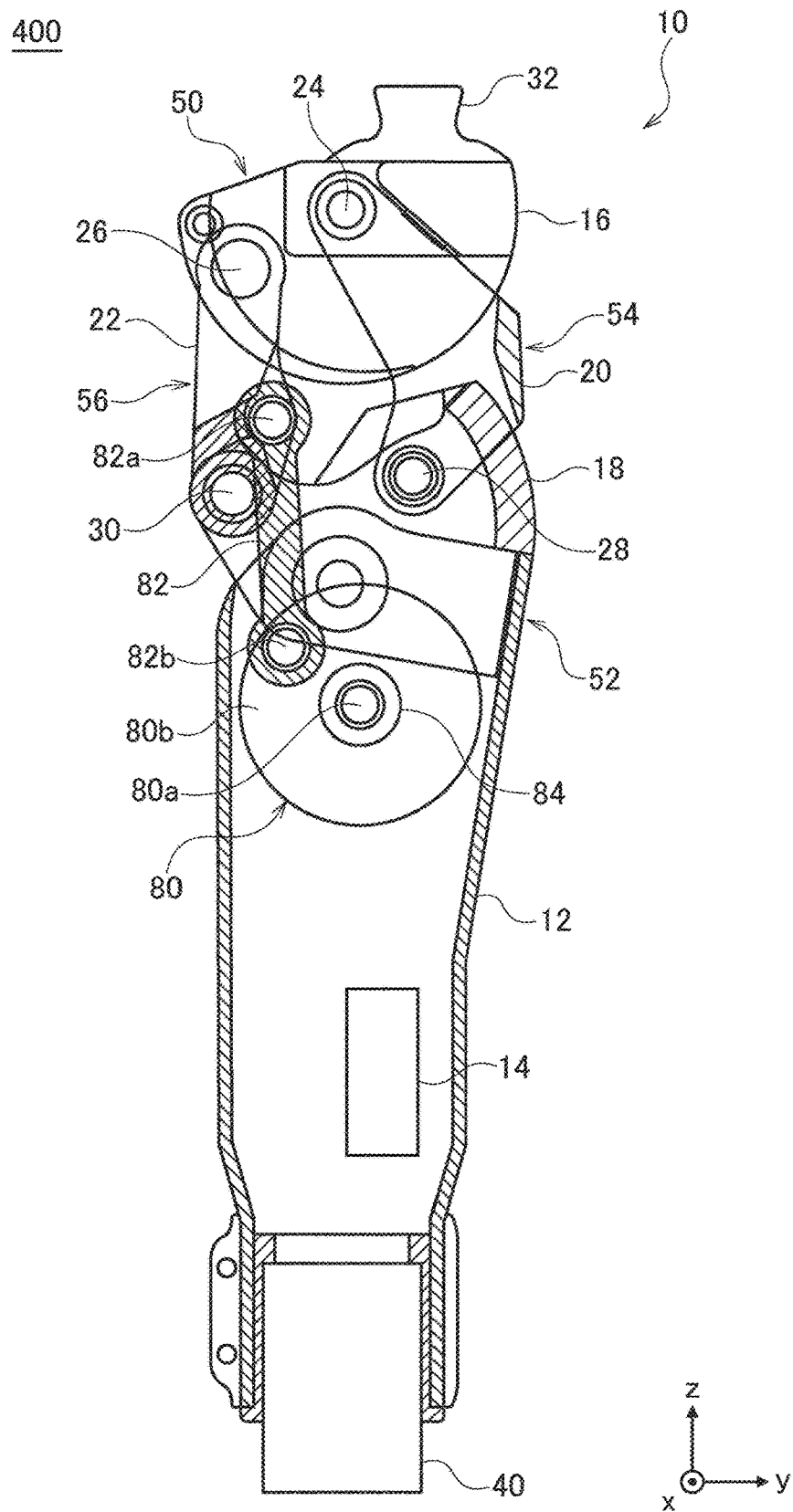
FIG. 8 is a schematic cross-sectional view of a multi-articulated link knee joint according to a fourth embodiment of the present invention.
Figure 9D:
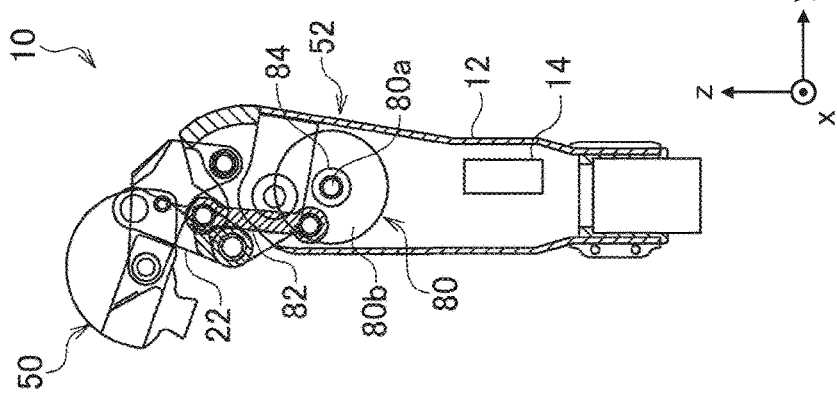
FIG. 9A to FIG. 9D are views illustrating how a knee unit is bent in the multi-articulated link knee joint according to the fourth embodiment.
Figure 9C:
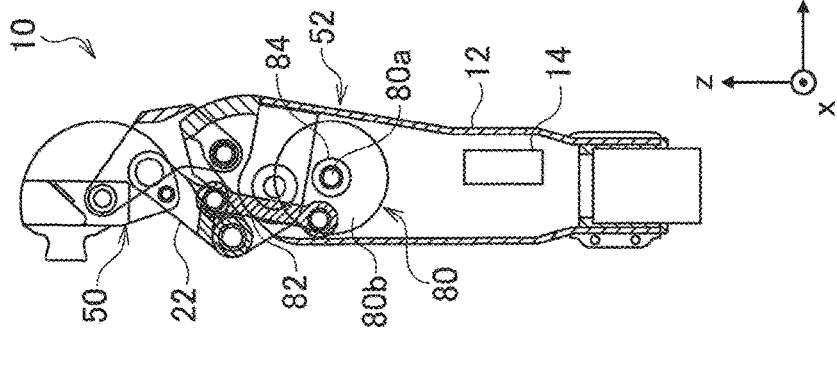
Figure 9B:
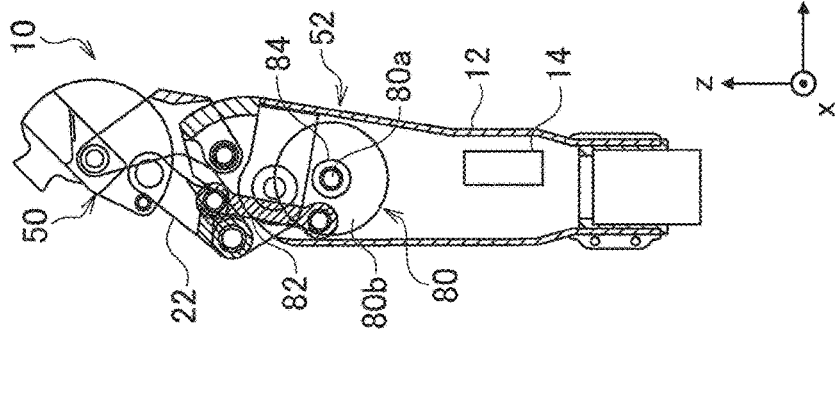
Figure 9A:
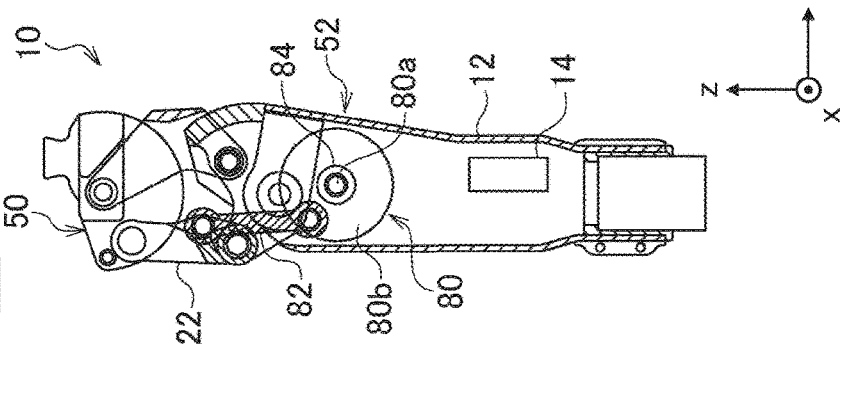

FIG. 8 is a schematic cross-sectional view of a multi-articulated link knee joint 400 according to a four embodiment of the present invention. The multi-articulated link knee joint 400 is different from the multi-articulated link knee joint 100 according to the first embodiment in that a rotary damper 80 is included as an auxiliary driver for assisting the motion of a knee unit 10.

The rotary damper 80 includes a disk-shaped rotator 80b rotatable about a rotary shaft 80a and an attenuator (not illustrated) for imparting a resistance against the rotation of the rotator 80b. The resistance imparted by the attenuator is controlled by a controller 44 of a control device 14. The rotary shaft 80a of the rotary damper 80 is attached to the lower leg part 12 so as to be parallel to the x axis.

The rotator 80b of the rotary damper 80 is coupled to a posterior link 22 via a damper link 82. More specifically, one end of the damper link 82 is rotatably attached to the posterior link 22 by an upper shaft 82a, and the other end of the damper link 82 is rotatably attached to the rotator 80b of the rotary damper 80 by a lower shaft 82b.

FIG. 9A to FIG. 9D are views illustrating how a knee unit 10 is bent in the multi-articulated link knee joint 400 according to the fourth embodiment. The bending angles of the knee unit 10 illustrated in FIG. 9A to FIG. 9D are 0°, 45°, 90°, and 160°, respectively. It is understood from FIG. 9A to FIG. 9D that when an upper link unit 50 rotates with respect to a lower link unit 52, the posterior link 22 rotates accordingly, and the rotator 80b of the rotary damper 80 rotates via the damper link 82 as the posterior link 22 rotates. By controlling the resistance against the rotation of the rotator 80b depending on the bending angle of the knee unit 10, the motion of the knee unit 10 can be assisted.

The multi-articulated link knee joint 400 according to the fourth embodiment includes a position detector 84 for detecting the rotation angle of the rotator 80b of the rotary damper 80. The position detector 84 is attached to an lower leg part 12 to detect the rotation angle of the rotator 80b with respect to the lower leg part 12. As the position detector 84, for example, a potentiometer, a rotary encoder, a resolver, or the like can be used.

The angle detector 42 (see FIG. 4) of the control device 14 obtains the bending angle from a detection value of the position detector 84. For example, when a table is generated in advance by measuring the relationship between the bending angle of the knee unit 10 and the detection value of the position detector 84, a bending angle of the knee unit 10 can be obtained from a detection value of the position detector 84 by referring to the table. The controller 44 (see FIG. 4) controls the rotary damper 80 in accordance with the bending angle to assist the motion of the knee unit 10.

Also in the multi-articulated link knee joint 400 according to the fourth embodiment, since it is not necessary to use a special device as the rotary damper 80, the bending angle of the knee unit 10 can be detected with a relatively reasonable configuration.

Moreover, in the multi-articulated link knee joint 400 according to the fourth embodiment, since the position detector 84 and the angle detector 42 (control device 14) are provided at the same portion (lower leg part 12), the wiring can be simplified.

In the fourth embodiment described above, the position detector 84 is attached to the lower leg part 12 to detect the rotation angle of the rotary damper 80 with respect to the lower leg part 12; however, the position detector 84 may be attached to the rotary damper 80 to detect the rotation angle of the rotary damper 80 with respect to the lower leg part 12.

Figure 10:
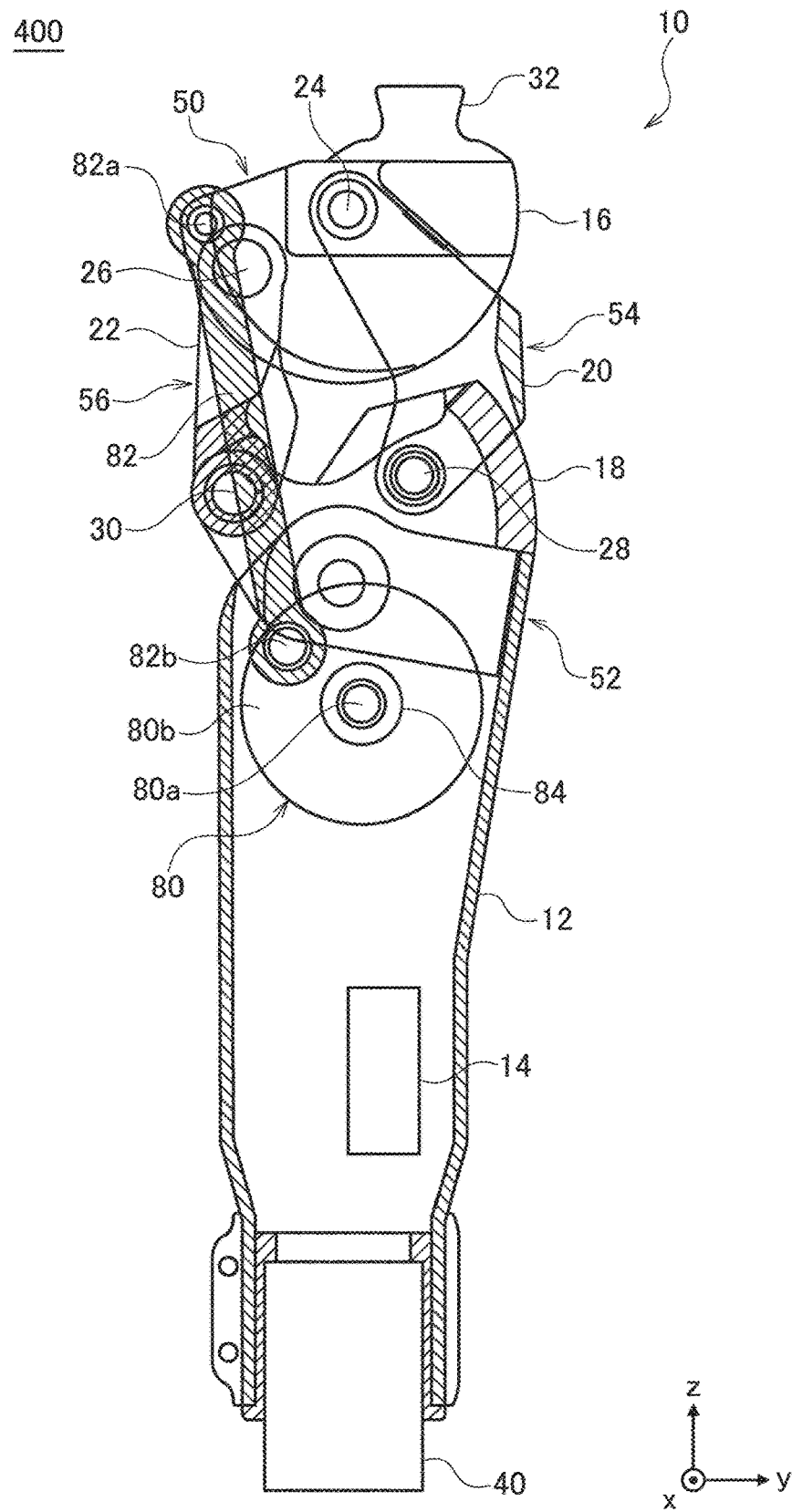
FIG. 10 is a schematic cross-sectional view of a first variation of the multi-articulated link knee joint according to the fourth embodiment of the present invention.

FIG. 10 is a view illustrating a first variation of the multi-articulated link knee joint 400 according to the fourth embodiment. In the embodiment illustrated in FIG. 8, the rotary damper 80 and the posterior link 22 are coupled by the damper link 82; however, the rotary damper 80 may be connected to another link. For example, as illustrated in FIG. 10, the rotator 80b of the rotary damper 80 may be coupled to the upper shaft 82a provided at the upper link 16 via the damper link 82.

Figure 11:
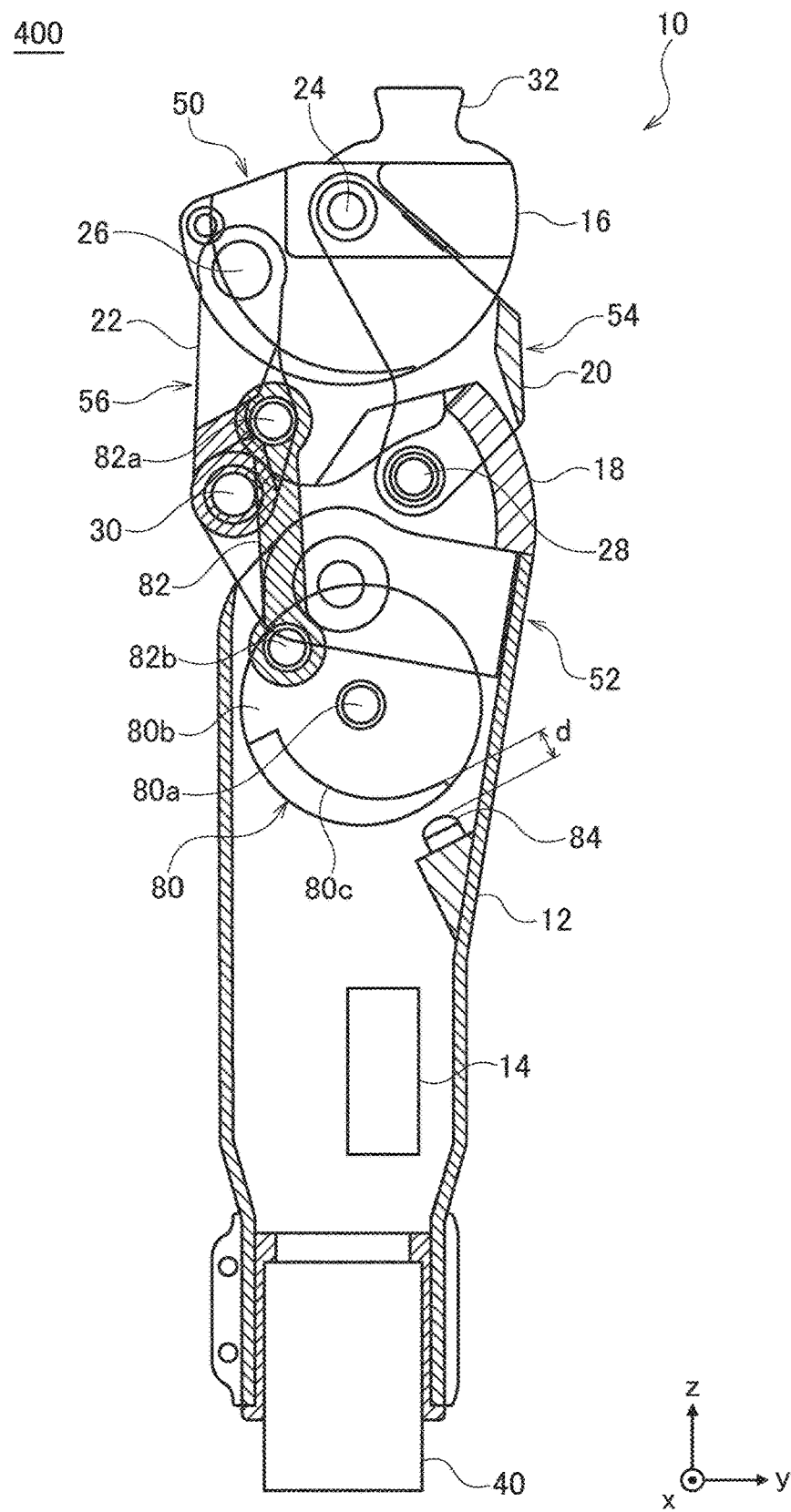
FIG. 11 is a schematic cross-sectional view of a second variation of the multi-articulated link knee joint according to the fourth embodiment of the present invention.

FIG. 11 is a view illustrating a second variation of the multi-articulated link knee joint 400 according to the fourth embodiment. In the embodiment illustrated in FIG. 8, as the position detector 84 for detecting the rotation angle of the rotator 80b of the rotary damper 80, a potentiometer, a rotary encoder, a resolver, etc. for directly detecting the rotation angle of the rotator 80b with respect to the lower leg part 12 haven been mentioned as examples; however, other methods can also be used.

In the second variation, a groove 80c is formed in the rotator 80b of the rotary damper 80. The groove 80c is formed on the outer circumferential surface of the rotator 80b so as to extend in an arc shape along the rotation direction of the rotator 80b. The groove 80c is formed such that the depth varies along the extending direction.

In the multi-articulated link knee joint 400 according to the second variation, the position detector 84 is attached to the lower leg part 12 to detect the distance d to the bottom of the groove 80c of the rotary damper 80. The position detector 84 may be, for example, an infrared sensor or an ultrasonic sensor. Since the depth of the groove 80c is formed such that the depth varies along the extending direction as described above, the detection value of the position detector 84 varies as the rotator 80b of the rotary damper 80 rotates. For example, when a table is generated in advance by measuring the relationship between the detection value of the position detector 84 and the rotation angle of the rotator 80b, a rotation angle of the rotator 80b can be detected indirectly from a detection value of the position detector 84 by referring to the table.

Figure 12:
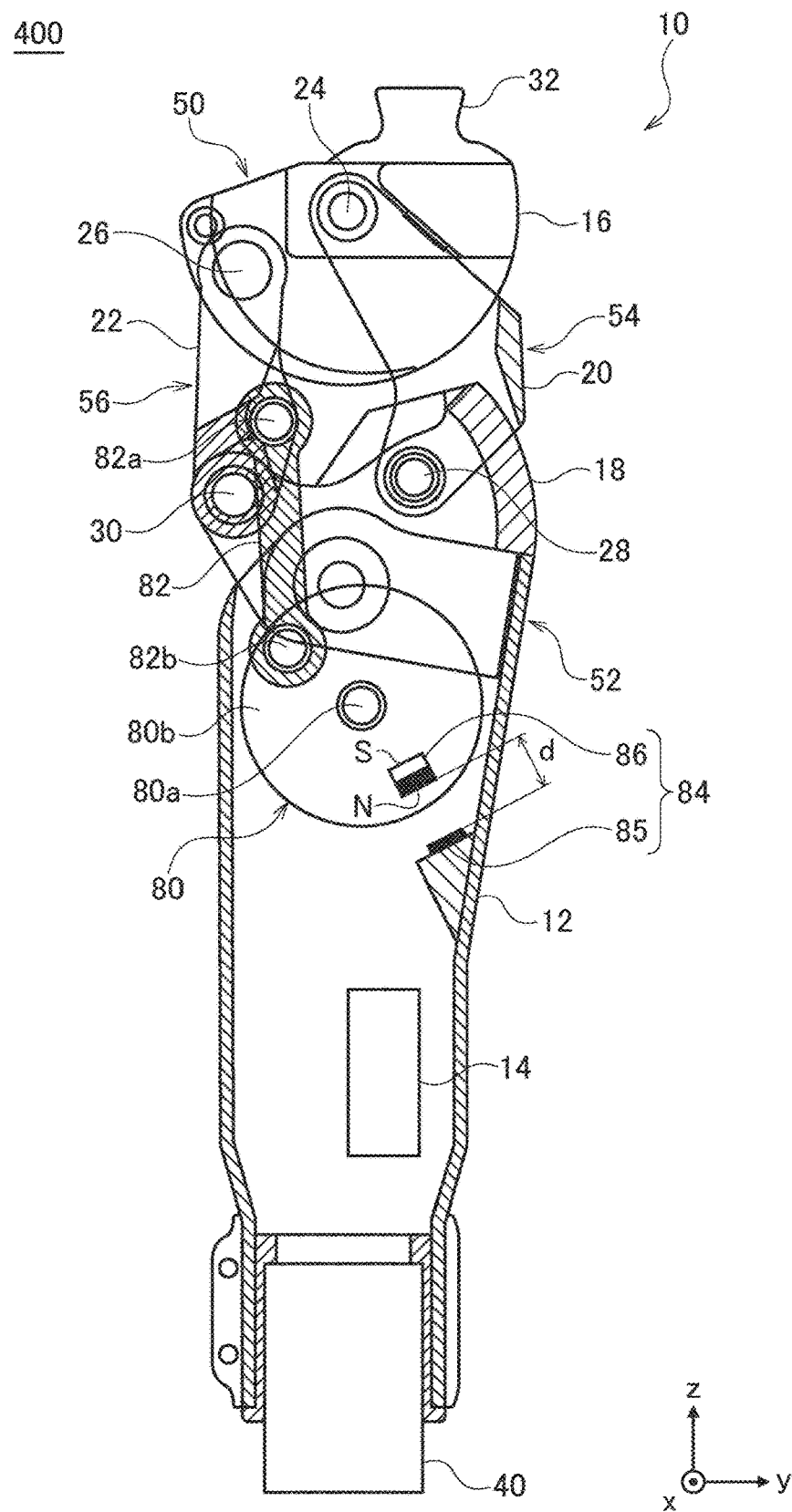
FIG. 12 is a schematic cross-sectional view of a third variation of the multi-articulated link knee joint according to the fourth embodiment of the present invention.

FIG. 12 is a view illustrating a third variation of the multi-articulated link knee joint 400 according to the fourth embodiment. In the third variation, the position detector 84 includes a magnet 85 and a magnetic sensor 86 that detects the intensity of the magnetic field generated by the magnet 85. The magnet 85 may be, for example, a rectangular alnico magnet. The magnetic sensor 86 may be, for example, a Hall element. The magnetic sensor 86 is provided at the rotator 80b of the rotary damper 80. The magnet 85 is provided at the lower leg part 12.

The magnetic sensor 86 provided at the rotator 80b outputs a detection value corresponding to the distance d to the magnet 85 provided at the lower leg part 12. The intensity of the magnetic field formed by the magnet 85 decreases as the distance from the magnet 85 increases. Therefore, the detection value of the magnetic sensor 86 varies as the rotator 80b of the rotary damper 80 rotates. For example, when a table is generated in advance by measuring the relationship between the detection value of the magnetic sensor 86 and the rotation angle of the rotator 80b, a rotation angle of the rotator 80b can be detected indirectly from a detection value of the magnetic sensor 86 by referring to the table.

Figure 13:
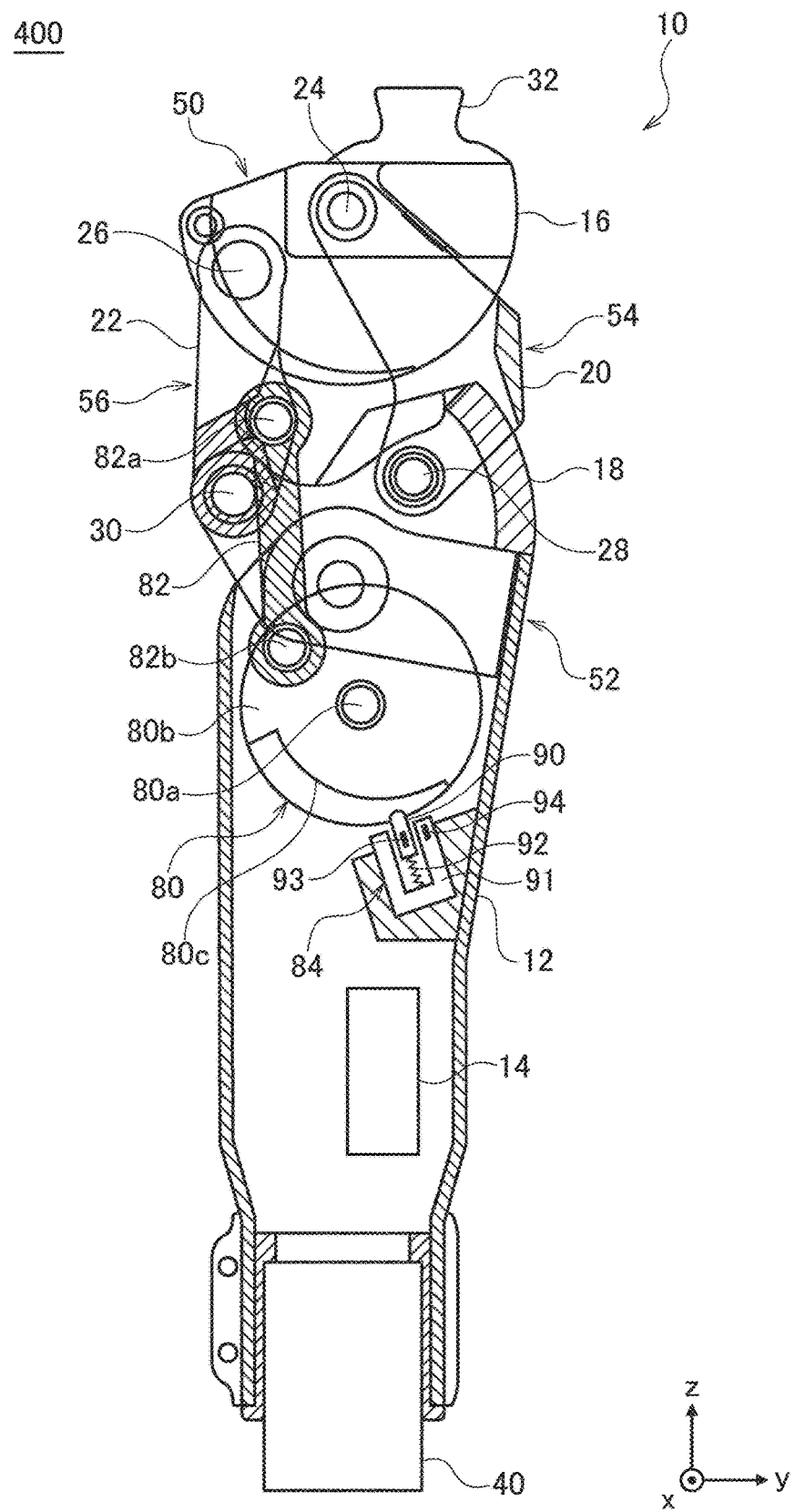
FIG. 13 is a schematic cross-sectional view of a fourth variation of the multi-articulated link knee joint according to the fourth embodiment of the present invention.

FIG. 13 is a view illustrating a fourth variation of the multi-articulated link knee joint 400 according to the fourth embodiment. In the fourth variation, the position detector 84 includes an abutting member 90, a case 91, a spring 92, a magnet 93, and a Hall element 94.

The case 91 has an accommodating space open upward. The case 91 is secured to the lower leg part 12. The abutting member 90 and the spring 92 are accommodated in the accommodating space of the case 91. The spring 92 energizes the abutting member 90 such that the upper portion of the abutting member 90 protrudes from the accommodating space. The magnet 93 is attached to the abutting member 90. The Hall element is attached to the case 91 and outputs a detection value corresponding to the distance to the magnet 93.

Moreover, in the fourth variation, a groove 80c is formed in the rotator 80b of the rotary damper 80. The groove 80c is formed on the outer circumferential surface of the rotator 80b so as to extend in an arc shape along the rotation direction of the rotator 80b. The groove 80c is formed such that the depth varies along the extending direction. The position detector 84 is attached to the lower leg part 12 such that the upper portion of the abutting member 90 fits into the groove 80c of the rotator 80b. The abutting member 90 is energized by the spring 92 and abuts against the bottom of the groove 80c. Therefore, the abutting member 90 moves as the rotator 80b of the rotary damper 80 rotates.

Due to the movement of the abutting member 90, the distance between the magnet 93 attached to the abutting member 90 and the Hall element 94 attached to the case 91 changes. That is, the detection value of the Hall element 94 varies as the rotator 80b of the rotary damper 80 rotates. For example, when a table is generated in advance by measuring the relationship between the detection value of the Hall element 94 and the rotation angle of the rotator 80b, a rotation angle of the rotator 80b can be detected indirectly from a detection value of the Hall element 94 by referring to the table.

The present invention has been described above on the basis of the embodiments. The embodiments are merely examples, and thus it should be understood by a person skilled in the art that combinations of components or processing processes of the examples may include various variations and that such variations are also within the scope of the present invention.

What is claimed is:

1. A multi-articulated link knee joint comprising:
   a knee unit in which an upper link unit is structured to rotate relative to a lower link unit by a multi-articulated link mechanism including a plurality of link units including the upper link unit, the lower link unit, and an additional link unit for coupling the upper link unit and the lower link unit;
   an auxiliary driver structured to assist motion of the knee unit and to move in accordance with rotation of the upper link unit;
   a position detector structured to detect a relative position of the auxiliary driver relative to the lower link unit; and
   an angle detector structured to obtain a bending angle of the knee unit from the detected relative position of the auxiliary driver,
   wherein the position detector detects a distance from the lower link unit to the auxiliary driver as the relative position of the auxiliary driver, and
   the angle detector obtains a bending angle of the knee unit from the detected distance.

2. The multi-articulated link knee joint according to claim 1, wherein the position detector and the angle detector are provided in the lower link unit.

* * * * *